United States Patent [19]

Alakhov et al.

[11] Patent Number: 5,698,529
[45] Date of Patent: Dec. 16, 1997

[54] CHEMOTHERAPEUTIC COMPOSITIONS

[75] Inventors: Valery Yu Alakhov, Baie d'Urfe, Canada; Alexander V. Kabonov, Moscow, Russian Federation; Peter G. Sveshnikov, Moscow, Russian Federation; Eugenii S. Severin, Moscow, Russian Federation

[73] Assignee: Supratek Pharma, Inc., Montreal, Canada

[21] Appl. No.: 659,437

[22] Filed: Jun. 6, 1996

Related U.S. Application Data

[63] Continuation of Ser. No. 374,406, Jan. 17, 1995, abandoned, which is a continuation of Ser. No. 957,998, Oct. 8, 1992, abandoned.

[51] Int. Cl.$^6$ ............ A61K 31/70; A61K 47/30; A61K 47/32; A61K 47/34

[52] U.S. Cl. ............ 514/34; 514/772.1
[58] Field of Search ............ 514/34, 772.1

[56] References Cited

PUBLICATIONS

Kabanov et al., J of Controlled Release, 22 (1992) 141–158.
The Merck Index, 9th Ed, Merck & Co., Inc., Rahway, N.J. 1976, p. 456.

*Primary Examiner*—Jerome D. Goldberg
*Attorney, Agent, or Firm*—Mathews, Collins, Shepherd & Gould, P.A.

[57] ABSTRACT

Compositions of anti-neoplastic agents incorporate the agent in micelles of at least one block copolymer of poly (oxyethylene)-poly(oxypropylene) in which the ratio of (oxypropylene) blocks to the (oxyethylene) blocks is from about 0.25 to about 1.5 and the micelles have an average diameter of from about 10 to about 25 nm.

5 Claims, No Drawings

CHEMOTHERAPEUTIC COMPOSITIONS

CROSS-REFERENCE TO RELATED APPLICATIONS

This is a continuation of Ser. No. 08/374,406 filed Jan. 17, 1995, now abandoned, which in turn is a continuation of Ser. No. 07/957,998, filed Oct. 8, 1992, now abandoned.

The present invention pertains to improvements in pharmaceutical compositions and in particular improvements in pharmaceutical compositions used in chemotherapy.

A number of anti-neoplastic agents currently are in use in chemotherapy (see generally "Cutting's *Handbook of Pharmacology*, 7th Ed., Chapter 13, Csáky and Barnes) and many additional agents are under investigation.

Because of their often complex structure, these agents can exhibit low stability in the blood stream. Many are extremely insoluble and possess poor transport properties with respect to cell membranes. In addition, binding of the anti-neoplastic agent with plasma proteins, as well as other nonspecific interactions in the blood stream prior to its reaching its target, can greatly reduce the effective amount actually available to combat the neoplastic cells. Moreover, multidrug resistance often is observed with such agents; i.e., the sensitivity of the neoplastic cells to the agent is observed to decrease, often by a factor of $10^3$, over the course of treatment and this resistance thereafter may manifest itself even with respect to structurally different anti-neoplastic agents.

In accordance with the present invention, the anti-neoplastic agent of choice (which may include a mixture of several distinct anti-neoplastic agents) is incorporated into a micelle of a block copolymer of poly(oxyethylene)-poly(oxypropylene) in an aqueous dispersion as hereinafter described.

The use of the block copolymer micelle in administrating the anti-neoplastic agent provides non-covalent solubilization which reduces water-instability and increases the solubility of the anti-neoplastic agent.

Moreover, while block copolymers of poly(oxyethylene)-poly(oxypropylene) have been used as nonionic surfactants, the effects observed here clearly extend beyond mere solubilization. For example, undesired pretarget protein binding of the anti-neoplastic agent is reduced; i.e., the anti-neoplastic agent appears to be "shielded" from proteins which otherwise would bind to it. Increased sensitivity with respect to the target anti-neoplastic cells also is observed. Finally a reversion in multidrug resistance is observed. While the multidrug resistance (MDR) phenomenon is not fully understood, it is accompanied by an overexpression of a transmembrane P-glycoprotein of $M_r$ about 170 kD (P-170) which mediates the ATP-dependent efflux of numerous drugs from such cells (although drug efflux may involve other membrane components of MDR cells as well). The present compositions appear to possess increased cytotoxic activity with respect to P-170 dependent and P-170 independent MDR cancer cells as compared with sensitive cells, thereby reducing the multidrug resistance effect.

A variety of anti-neoplastic agents are suitable for use in the present composition. These include alkaloids such as vinblastine, colchicine, and demecoline; antibiotics such as those of the rhodomycin group as for example as daunorubicin and doxorubicin, those of the mitomycin group as for example mitomycin C and N-methyl mitomycin C, and those of the bleomycin group such as bleomycin $A_2$; and antifolates such as methotrexate, aminopterin, and dideaza-tetrahydrofolic acid. It will be appreciated that this improvement extends to mixtures of several such agents.

The present invention is not directed to the underlying anti-neoplastic activity of these agents but rather to an improvement in the manifestation of this activity through formulation.

The block copolymers of poly(oxyethylene)-poly(oxypropylene) generally are characterized by the structural formula:

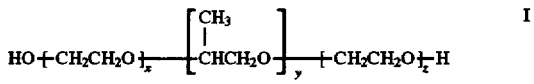

in which each of x and z, independently of the other, has a value of from about 5 to about 100 and y has a value of from about 20 to about 80. Such block copolymers are known (see Stanton, *Am. Perfumer. Cosmet.* 72(4), 54–58 (1958); Schmolka, *Loc. cit.* 82(7), 25–30 (1967); and *Nonionic Surfactants*, Schick, Ed., (Dekker, NY, 1967) 300–371. A number of these copolymers are commercially available under the generic names of "poloxamers" and "pluronics".

The hydrophobic/hydrophilic properties of a given block copolymer depends upon the ratio of the number of oxypropylene groups to the number of oxyethylene groups. For a composition containing a single block copolymer of poly(oxyethylene)-poly(oxypropylene), for example, this relationship, taking into account the molecular masses of the central hydrophobic block and the terminal hydrophilic blocks, can be expressed as follows:

$$n = \frac{y}{x+z} * 1.32$$

in which y is the number of oxypropylene units and x and z are number of oxyethylene units.

Selecting a block copolymer with the appropriate n value depends upon the hydrophobic/hydrophilic properties of the specific anti-neoplastic agent, or the composite hydrophobic/hydrophilic properties of a mixture of anti-neoplastic agents, to be formulated. Typically n will range in value from about 0.25 to about 1.5. This range should be viewed not as numerically critical but as expressing the optimum hydrophobic-hydrophilic balance between the predominantly hydrophilic poly(oxyethylene) blocks and the predominantly hydrophobic poly(oxypropylene) blocks.

An important aspect of the present invention involves utilizing mixture of different block copolymers of poly(oxyethylene)-poly(oxypropylene) to achieve a more specific hydrophobic-hydrophilic balance suitable for a given anti-neoplastic agent or mixture of several anti-neoplastic agents, preserving the optimal size of particles. For example, a first block copolymer may have an n of 1.00 whereas a second may have a value of 1.5. If material having an n of 1.3 is desired, a mixture of one weight portion of the first block copolymer and 1.5 weight portion of the second block copolymer can be employed.

A more generalized relationship therefore for such mixtures can be expressed as follows:

$$N = \frac{y_1 * a}{(x_1 + z_1) * (a+B)} + \frac{y_2 * a}{(x_2 + z_2) * (a+b)} * 1.32$$

in which:

$y_1$ and $y_2$ and the number of oxypropylene units in the first and second block copolymers, respectively;

$x_1$ and $z_1$ are number of oxyethylene units in the first block copolymer;

$x_2$ and $z_2$ are number of oxyethylene units in the second block copolymer;

a is the weight proportion in the first block copolymer; and b is the weight proportion in the second block copolymer.

If only one block copolymer of poly(oxyethylene)-poly (oxypropylene) is utilized, N will equal n. An analogous relationship will apply to compositions employing more than two block copolymers of poly(oxyethylene)-poly (oxypropylene).

Using the above parameters, one or more block copolymers of poly(oxyethylene)-poly(oxypropylene) are combined so as to have a value for N of from about 0.25 to about 1.5. The combined copolymers form micelles, the value of N affecting in part the size of the micelles thus produced. Typically the micelles will have an average diameter of from about 10 to about 25 nm., although this range can vary widely. The average diameter of any given preparation can be readily determined by quasielastic light scattering techniques.

The anti-neoplastic compound or compounds in the copolymer micelle are administered parenterally in aqueous formulations, alone or in combination with other therapeutic agents including other anti-neoplastic agents, steroids, etc., to a mammal suffering from neoplasm and in need of treatment. Parenteral routes of administration include intramuscular, intrathecal, intraperitoneal, intravenous and intra-arterial. Isotonic micellar solution of one or more block copolymers of poly(oxyethylene)-poly(oxypropylene) incorporating one or more anti-neoplastic agents are used for parenteral administration. Dosages typically are those associated with the specific anti-neoplastic agent, although as in every case the regimen must be titrated to the particular neoplasm, the condition of the patient, and the response. For example, an isotonic micellar solution of daunorubicin in the block copolymer micelles is administered so as to provide about 1 mg of daunorubicin per kg of body weight. Vinblastine on the other hand is administered in the same fashion but in accordance with conventional usage at lower doses of from about 0.1 to about 0.2 mg/kg. Often the amount required can be reduced.

The following examples will serve to further typify the nature of the invention but should not be construed as a limitation on the scope thereof which is defined solely by the appended claims.

EXAMPLE 1

A. A block copolymer of poly(oxyethylene)-poly (oxypropylene) in which N=0.25 (Pluronic F-68) is diluted with RPMI 1640 medium to a final concentration of 2.0% at 4° C. The mixture is incubated for 30 minutes at 37° C. and then sterilely filtered through a 0.22 μm filter. An equal volume of a solution of 200 μg daunorubicin in RPMI 1640 medium is added and this mixture is incubated for 30 minutes at 37° C.

B. Human ovarian carcinoma cells (CRL157) are precultured in 1% solution of the same block copolymer but without daunorubicin in RPMI 1640 medium supplemented with 10% calf fetal serum. The preparation of part A is added and the mixture is incubated for 60 minutes at 37° C. and the cells then washed three times with RPMI 1640 and cultured in RPMI 1640 supplemented with 10% calf fetal serum for 3 days {Prep. A}. Cytotoxicity is measured, both for this preparation and a parallel preparation of free daunorubicin {Prep. B}, using the method of Alley et al., *Cancer Res.*, 48, 589–601 (1988). The results are as follows:

|         | conc. (ng/mL) |       |      |     |    |    |
|---------|---------------|-------|------|-----|----|----|
|         | 50000         | 10000 | 2000 | 400 | 80 | 16 |
|         | % Inhibition  |       |      |     |    |    |
| Prep. A | 100           | 100   | 92   | 24  | 6  | 2  |
| Prep. D | 100           | 81    | 53   | 38  | 20 | 1  |

Following the same procedure, cytotoxicity is determined against human T-lymphoma (Jurkat) cells:

|         | conc. (ng/mL) |       |      |     |    |    |     |
|---------|---------------|-------|------|-----|----|----|-----|
|         | 50000         | 10000 | 2000 | 400 | 80 | 16 | 3.2 |
|         | % Inhibition  |       |      |     |    |    |     |
| Prep. A | 100           | 100   | 100  | 100 | 92 | 33 | 3   |
| Prep. B | 100           | 100   | 100  | 84  | 51 | 44 | 22  |

Following the same procedure, cytotoxicity is determined against human small cell carcinoma of lung (H-69):

|         | conc. (ng/mL) |       |      |     |     |    |     |
|---------|---------------|-------|------|-----|-----|----|-----|
|         | 50000         | 10000 | 2000 | 400 | 80  | 16 | 3.2 |
|         | % Inhibition  |       |      |     |     |    |     |
| Prep. A | 100           | 100   | 100  | 100 | 100 | 42 | 12  |
| Prep. B | 100           | 100   | 100  | 91  | 69  | 42 | 20  |

EXAMPLE 2

Block copolymers of poly(oxyethylene)-poly (oxypropylene) having the ratios of poly(oxypropylene) to poly(oxyethylene) indicated below are dispersed in RPMI 1640 medium at the concentration indicated below. The mixtures are incubated for 40 minutes at 30° C. The average micelle diameter is measured by quasielastic light scattering and the value of N calculated as previously indicated. The results are as follows:

| copolymer        | conc. | Avg. Diameter | N    |
|------------------|-------|---------------|------|
| F-68[1]          | 1.0%  | 726.0nm       | 0.25 |
| P-85[2]          | 1.0%  | 18.0nm        | 1.00 |
| L-64[3]          | 1.0%  | 20.4nm        | 1.50 |
| 1:1.5 P-85:L-64  | 0.01% | 17.0nm        | 1.30 |
| 1:2.5 F-68:L-64  | 1.0%  | 33.5nm        | 1.38 |

Note 1: $x = 80$, $y = 30$, and $z = 80$
Note 2: $x = 75/2$, $y = 55$, and $z = 75/2$
Note 3: $x = 27/2$, $y = 30$, and $z = 27/2$

Example 3

A. A 1:1.5 mixture of block copolymers of poly (oxyethylene)-poly(oxypropylene) (pluronics P-85 and L-64) having individual ratios (n) of (oxypropylene) to (oxyethylene) blocks of 1.00 and 1.50, respectively, and a combined value (N) of 1.30, is diluted with RPMI 1640 medium to a final concentration of 2.0% at 4° C. The mixture is incubated for 30 minutes at 37° C. and then sterilely filtered through a 0.22 μm filter. An equal volume of a solution of 200 μg daunorubicin in RPMI 1640 medium is added and this mixture is incubated for 30 minutes at 37° C.

B. Cytotoxicity to human ovarian cancer cells (CRL157) is measured, both for this preparation {Prep. A} and a parallel preparation of free daunorubicin {Prep. B} as described in Example 1B. The results are as follows:

| | conc. (ng/mL) | | | | | | |
|---|---|---|---|---|---|---|---|
| | 50000 | 10000 | 2000 | 400 | 80 | 16 | 3.2 |
| | | | % Inhibition | | | | |
| Prep. A | 100 | 100 | 100 | 100 | 94 | 53 | 8 |
| Prep. B | 100 | 100 | 81 | 50 | 29 | 10 | 2 |

EXAMPLE 4

Daunorubicin in the composition of Example 3 is evaluated for cytotoxicity in (i) human T-lymphoma (Jurkat) cells as described in Example 1 and (ii) normal human mononuclear cells. The results are as follows:

| | | conc. (ng/mL) | | | | | | |
|---|---|---|---|---|---|---|---|---|
| Cell | | 50000 | 10000 | 2000 | 400 | 80 | 16 | 3.2 |
| | | | | % Inhibition | | | | |
| Prep. A | Jur. | 100 | 100 | 100 | 100 | 100 | 74 | 28 |
| Prep. B | Jur. | 100 | 100 | 100 | 83 | 59 | 36 | 21 |
| Prep. A | Norm. | 100 | 100 | 91 | 60 | 21 | 5 | 2 |
| Prep. B | Norm. | 100 | 100 | 80 | 58 | 23 | 18 | 1 |

EXAMPLE 5

$IC_{50}$ values for (i) human T-lymphoma (Jurkat) cells and (ii) normal human mononuclear cells are determined for the daunorubicin composition of Example 3 and compared to those for free daunorubicin. Measurements are made at the indicated intervals of the drug contact with the cells from 15 minutes to 12 hours. The results are as follows:

| | | time (hours) | | | | | | | |
|---|---|---|---|---|---|---|---|---|---|
| | Cell | 0.25 | 0.50 | 0.75 | 1.0 | 2.0 | 4.0 | 8.0 | 12 |
| | | | | | $IC_{50}$ (ng/mL) | | | | |
| Prep. A | Jur. | 150 | 46 | 25 | 17 | 9.0 | 0.80 | 0.50 | 0.30 |
| Prep. B | Jur. | 120 | 68 | 35 | 25 | 19 | 16 | 3.0 | 5.2 |
| Prep. A | Norm. | 3570 | 950 | 620 | 450 | 250 | 220 | 160 | 140 |
| Prep. B | Norm. | 4900 | 980 | 405 | 310 | 290 | 275 | 280 | 240 |

EXAMPLE 6

The antineoplastic agent vinblastine is incorporated into the block copolymer mixture described in Example 3. The $IC_{50}$ of this preparation against $SKVO_3$ cells, a drug-sensitive human ovarian carcinoma line, is determined to be 0.121 µg/mL; the $IC_{50}$ against SKVLB cells, an MDR subline expressing high levels of P-170 obtained through long term cultivation of $SKVO_3$ in the presence of vinblastine, is 0.0012 µg/mL. The $IC_{50}$ of free vinblastine against $SKVO_3$ cells is determined to be 0.095 µg/mL; the $IC_{50}$ against SKVLB cells is 0.615 µg/mL.

EXAMPLE 7

The antineoplastic agent mitomycin C is incorporated into the block copolymer mixture described in Example 3. The $IC_{50}$ of this preparation against $SKVO_3$ cells is determined to be 0.265 µg/mL; the $IC_{50}$ against SKVLB cells is 0.005 µg/mL. The $IC_{50}$ of free mitomycin against $SKVO_3$ cells is determined to be 0.320 µg/mL; the $IC_{50}$ against SKVLB cells is 1.120 µg/mL.

EXAMPLE 8

The antineoplastic agent methotrexate is incorporated into the block copolymer mixture described in Example 3. The $IC_{50}$ of this preparation against $SKVO_3$ cells is determined to be 0.880 µg/mL; the $IC_{50}$ against SKVLB cells is 0.0175 µg/mL. The $IC_{50}$ of free methotrexate against $SKVO_3$ cells is determined to be 1.090 µg/mL; the $IC_{50}$ against SKVLB cells is 1.340 82 g/mL.

EXAMPLE 9

The antineoplastic agent colchicine is incorporated into the block copolymer mixture described in Example 3. The $IC_{50}$ of this preparation against $SKVO_3$ cells is determined to be 0.720 µg/mL; the $IC_{50}$ against SKVLB cells is 0.045 µg/mL. The $IC_{50}$ of free colchicine against $SKVO_3$ cells is determined to be 0.950 µg/mL; the $IC_{50}$ against SKVLB cells is 7.450 µg/mL.

EXAMPLE 10

The antineoplastic agent daunorubicin is incorporated into the block copolymer mixture described in Example 3. The $IC_{50}$ of this preparation against $SKVO_3$ cells is determined to be 0.600 µg/mL; the $IC_{50}$ against SKVLB cells is 0.0068 µg/mL. The $IC_{50}$ of free daunorubicin against $SKVO_3$ cells is determined to be 0.620 µg/mL; the $IC_{50}$ against SKVLB cells is 5.850 µg/mL.

EXAMPLE 11

To 30 µL of a 20 mg/mL solution of bovine serum albumin in phosphate buffered saline are added 30 µL of daunorubicin solution in the block copolymer mixture described in Example 3 {Prep. A}. A second formulation {Prep. B} is prepared in parallel fashion using free daunorubicin.

The preparations are incubated for 10 minutes at 25° C. and then analyzed by HPLC on a TSK-3000 SW gel-filtration column in PBS containing 0.3 M sodium chloride and 5% acetonitrile. Detection is performed at 280 nm and 470 nm. The portion of the drug bound with BSA is determined as:

$$D_b = S_b/S_f$$

in which:

$S_b$ is relative area of the 470 nm peak (corresponding to daunorubicin) which coincides in retention time for the 280 nm peak (corresponding to BSA); and $S_f$ is relative area of the peak (or peaks) corresponding to daunorubicin which does not coincide in retention time of the BSA peak.

The results are as follows:

| Composition | $D_b$ |
|---|---|
| Prep. A | 0.01 |
| Prep. B | 0.39 |

EXAMPLE 12

Micellar daunorubicin obtained as described in Example 3 {Prep. A} and free daunorubicin {Prep. B} are incubated in the dark at 37° C. and cytotoxicity to CRL157 cells in then determined in the manner discussed in Part B of Example 1.

The results are as follows:

|  | time (hours) | | | | | |
|---|---|---|---|---|---|---|
|  | 2 | 4 | 12 | 24 | 48 | 96 |
|  | | | $IC_{50}$, µg/mL | | | |
| Prep. A | 9.1 | 10.05 | 9.8 | 10.4 | 10.7 | 11.3 |
| Prep. B | 400 | 475 | 1120 | 6300 | 10180 | 48900 |

EXAMPLE 13

The daunorubicin composition of Example 3 {Prep. A} is evaluated against daunorubicin-sensitive human breast cancer (MCF-7) and two cell lines demonstrating resistance: daunorubicin/verapamil-resistant (MCF-7AU) not expressing P-170, and daunorubicin-resistant, verapamil-sensitive (Dox-MCF-7), expressing P-170, in each case in comparison to free daunorubicin {Prep. B}. The results are as follows:

|  | conc. (ng/mL) | 50000 | 10000 | 2000 | 400 | 80 | 16 |
|---|---|---|---|---|---|---|---|
|  | Cell | | | % Inhibition | | | |
| Prep. A | MCF-7 | 100 | 100 | 84 | 65 | 42 | 12 |
|  | MCF-7AU | 100 | 100 | 100 | 96 | 69 | 39 |
|  | Dox-MCF-7 | 100 | 100 | 100 | 89 | 73 | 45 |
| Prep. B | MCF-7 | 100 | 100 | 91 | 69 | 43 | 15 |
|  | MCF-7AU | 100 | 89 | 65 | 37 | 9 | 3 |
|  | Dox-MCF-7 | 100 | 86 | 62 | 39 | 7 | 2 |

Free daunorubicin {Prep. B} exhibits higher $IC_{50}$'s (is less toxic) against both resistant lines. Daunorubicin incorporated in the block copolymers {Prep. A} exhibited lower $IC_{50}$'s (is more toxic) against both resistant lines.

EXAMPLE 14

Groups (6 animals/dose point) of C57B1/6 7-week-old female mice are inoculated i.p. with free or micellar (N=1.3) daunorubicin obtained as described is Example 3 {Prep. B and Prep. A, respectively}, and are observed for 14 days. Drug concentrations are adjusted so that a maximum volume of 0.5 mL is injected in each mouse.

The MTD is defined as a dose which leads to no daunorubicin-deaths (any higher dose leads to the daunorubicin-related death of at least 1 animal per group). The experiment is repeated twice. The results are reproducible with less that 10% variation.

The MTD of free and micellar (N=1.3) daunorubicin is determined to be 2.0 and 1.0 µg/kg body weight, respectively.

EXAMPLE 15

Daunorubicin possesses high specificity with respect to bone marrow, manifesting itself as reversible leukopenia, i.e., a decrease in the number of WBS (leukocyte count) during drug administration. Bone marrow suppression, as well as anticancer effects of daunorubicin, are conditioned by DNA-intercollating activity, whereas the most harmful side effect of anthracyclines, cardiotoxicity, results mainly from membrane interactions with metabolites (which have low anticancer activity and do not produce significant effects on bone marrow). Therefore, the leukocyte count during in vivo administration of MTD daunorubicin allows the assessment of the ratio between specific (DNA-intercollation) activity of the drug and non-specific toxicity.

Groups (6 animals/group) of C57B1/6 7-week-old female mice are inoculated i.p. with free of micellar (N=1.3) daunorubicin obtained as described in Example 3 {Prep. B and Prep. A, respectively}. Drug concentrations (MTD) are adjusted so that a maximum volume of 0.5 mL is injected in each mouse. Blood samples are collected and viable leukocytes are counted as described in Michisch et al., *Proc. Natl. Acad. Sci. USA* 88, 547–551 (1991). The number of WBC after administration of 0.1 mL PBS, 15–16 mln cells/mL, is used as the control. The experiment is repeated twice. The results are reproducible with less than 10% variation.

The results obtained are as follows:

|  | Days | | | | |
|---|---|---|---|---|---|
|  | 0 | 3 | 7 | 10 | 14 |
|  | | WBS, % of control | | | |
| Prep. A | 100 | 20 | 46.6 | 86.6 | 100 |
| Prep. B | 100 | 40 | 60 | 93.8 | 100 |

EXAMPLE 16

The effects of free and micellar daunorubicin obtained as described in Example 3 {Prep. B and Prep. A, respectively} on leukocyte count are determined three days after administration as described in Example 15.

The results obtained are as follows:

| Dose of daunorubicin % of MTD | 25 | 50 | 75 | 100 |
|---|---|---|---|---|
|  | | WBS, % of control | | |
| Prep. A | 85 | 73 | 45 | 21 |
| Prep. B | 78 | 61 | 36 | 39 |

The data shown in Examples 14 through 16 indicate that solubilization of daunorubicin in the block copolymer micelles does not essentially affect the drug's overall toxicity (MTD of 2 mg/kg and 1 mg/kg for free and micellar drug, respectively), whereas an increase in reversible bone marrow suppression is observed which does not markedly influence the animal survivability.

EXAMPLE 17

Anti-neoplastic activity is determined by evaluation of the cytotoxic activity of plasma of mammals inoculated with the test composition (see de Valeriola et el., *Cancer Chemother. Pharmacol.* 29, 133–140, 1991).

Groups (6 animals/group) of C57B1/6 7-week-old female mice are inoculated i.v. (via the tail vein) with free or micellar (N=1.3) daunorubicin obtained as described in Example 3 {Prep. B and Prep. A, respectively}. Drug concentrations (MTD) are adjusted so that a maximum volume of 0.1 mL is injected in each mouse. The experiment is repeated twice. The results are reproducible with less than 10% variation.

To obtain plasma samples, blood (10 μl) is collected from the tail artery one hour after drug administration, diluted 1:10 with sterile RPMI 1640 medium, and centrifuged at 400 g for 15 minutes. The supernatants obtained are diluted as shown in the table with plasma analogously obtained from mice not inoculated with the drug (the plasma of mice not inoculated with the drug does not produce any significant cytotoxic effect on H-69 cells) and mixed with an equal volume of H-69 cell suspension on RPMI 1640 medium supplemented with 10% fetal calf serum. The cells are incubated for two hours at 37° C. and 5% $CO_2$, and then washed three times with RPMI 1640. The pretreated cells are incubated in RPMI 1640 supplemented with 10% fetal calf serum at 37° C. and 5% $CO_2$ for three days, after which cytotoxicity is determined as described in Example 1.

The results obtained are as follows:

|  | Dilution of plasma | | | |
|---|---|---|---|---|
|  | 1:20 | 1:200 | 1:2000 | 1:20000 |
|  |  | Inhibition, % | | |
| Prep. A | 100 | 58 | 8 | 0 |
| Prep. B | 42 | 5 | 0 | 0 |

Thus cytotoxic titers, the dilution at which the plasma of mice inoculated with preparations B or A produced 50% inhibition of H-69 cell growth, of plasma of mice inoculated with preparations B and A with respect to H-69 cells are determined to be 1:228 and 1:48, respectively.

EXAMPLE 18

The procedure of Example 16 is repeated utilizing SKVLB and $SRVO_3$ cells. The results are as follows:

a) when MTD of daunorubicin is introduced

|  |  | Inhibition, % | | |
|---|---|---|---|---|
| Plasma Dilution |  | 1:20 | 1:200 | 1:2000 |
| Prep. A | SKVLB | 82 | 61 | 18 |
| Prep. B | SKVLB | 0 | 0 | 0 |
| Prep. A | $SKVO_3$ | 11 | 0 | 0 |
| Prep. B | $SRVO_3$ | 9 | 0 | 0 | b) when 10 mg/kg daunorubicin are introduced

|  |  | Inhibition, % | | |
|---|---|---|---|---|
| Plasma Dilution |  | 1:20 | 1:200 | 1:2000 |
| Prep. A | SKVLB | 100 | 94 | 69 |
| Prep. B | SKVLB | 8 | 0 | 0 |
| Prep. A | $SKVO_3$ | 62 | 31 | 0 |
| Prep. B | $SRVO_3$ | 22 | 6 | 0 |

EXAMPLE 19

A composition suitable for parental administration is prepared by dissolving 400 mg of Pluronic P-85 and 600 mg of Pluronic L-64 in 50 mL of RPMI 1640 at 4° C. The mixture is incubated for 30 minutes at 37° C. and then sterilely filtered through a 0.22 μm filter. This is mixed with a solution of 10 mg of sterile lyophilized daunorubicin powder dissolved in 50 mL of RPMI and incubated for 30 minutes at 37° C.

The composition can be stored in the dark at room temperature for 7 days without any essential loss of activity or can be lyophilized and stored for at least 1 year in the dark at room temperature.

EXAMPLE 20

A further composition suitable for parental administration is prepared by dissolving 400 mg of Pluronic P-85 and 600 mg of Pluronic L-64 in 50 mL of PBS at 4° C. The mixture is incubated for 30 minutes at 37° C. and then sterilely filtered through a 0.22 μm filter. This is mixed with a solution of 1 mg of sterile lyophilized daunorubicin powder and 5 mg of glucose dissolved in 50 mL of PBS and the mixture is incubated for 30 minutes at 37° C.

The composition can be stored in the dark at room temperature for 7 days without any essential loss of activity or can be lyophilized and stored for at least 1 year in the dark at room temperature.

EXAMPLE 21

A further composition suitable for parental administration is prepared by dissolving 100 mg of sodium ascorbate in a 9% aqueous solution of sodium chloride. To one-half of this solution are added at 4° C. 400 mg of Pluronic P-85 and 600 mg of Pluronic L-64. The mixture is incubated for 30 minutes at 37° C. and then sterilely filtered through a 0.22 μm filter. Separately 10 mg of sterile lyophilized daunorubicin powder and 50 mg of glucose are dissolved in the remaining sodium ascorbate-sodium chloride solution and the two solutions are mixed and incubated for 30 minutes at 37° C.

This composition can be stored for 30 days in the dark at room temperature without any essential loss of activity or can be lyophilized and stored for at least 1 year in the dark at room temperature.

What is claimed is:

1. The method of combating the growth of cancer cells in a mammal through administration of a rhodamycin antibiotic selected from the group consisting of daunorubicin and doxorubicin leading to a reduction in multidrug resistance which comprises administering to said mammal an effective amount of said rhodamycin antibiotic in micelles comprising at least one block copolymer, each of said block copolymer having of the formula:

$$HO\text{-}(CH_2CH_2O)_x\text{-}[CHCH_2O]_y\text{-}(CH_2CH_2O)_z\text{-}H$$
$$\phantom{HO\text{-}(CH_2CH_2O)_x\text{-}[}|\phantom{HCH_2O]_y\text{-}(CH_2CH_2O)_z\text{-}H}$$
$$\phantom{HO\text{-}(CH_2CH_2O)_x\text{-}[}CH_3$$

in which x and z have values of from about 5 to about 100 and y has a value of from about 20 to about 80, such that in the expression:

$$N = \left[ \frac{y_1{}^{*a}}{(x_1+z_1)*(a+b)} + \frac{y_2{}^{*a}}{(x_2+z_2)*(a+b)} \right] * 1.32$$

where $x_1$, $z_1$, and $y_1$ correspond to x, z, and y, respectively, of a first block copolymer, a is the weight proportion of said first block copolymer, and if an additional block copolymer is present, $x_2$, $z_2$, and $y_2$ correspond to x, z, and y, respectively, of said additional block copolymer, and b is the weight proportion of said additional block copolymer, the variable N has a value of from about 0.25 to about 1.5.

2. The method according to claim 1 wherein said micelles comprise a single block copolymer.

3. The method according to claim 1 wherein N has a value of about 1.

4. The method according to claim 1 wherein said rhodamycin antibiotic is daunorubicin.

5. The method according to claim 1 wherein said rhodamycin antibiotic is doxorubicin.

* * * * *

UNITED STATES PATENT AND TRADEMARK OFFICE
CERTIFICATE OF CORRECTION

PATENT NO. : 5,698,529
DATED : Dec. 16, 1997
INVENTOR(S) : Valery Yu Alakhov et al.

It is certified that error appears in the above-identified patent and that said Letters Patent is hereby corrected as shown below:

Title page,
        item   [75], inventor "Alexander V. Kabonov" should read "Alexander V. Kabanov".

Signed and Sealed this

Seventh Day of April, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,698,529
DATED : Dec. 16, 1997
INVENTOR(S) : Valery Yu. Alakhov et al.

It is certified that error appears in the above-identified patent and that said Letters Patent is hereby corrected as shown below:

In Column 9, line 35 (Example 18), "SRVO3" should be changed to "S$\underline{K}$VO3".

In Column 2 (line 60), and in Column 10 (line 55), the formula should read as follows:

$$N = \left[ \frac{y_1 * a}{(x_1 + z_2) * (a+b)} + \frac{y_2 * b}{(x_2 + z_2) * (a+b)} \right] * 1.32$$

Signed and Sealed this

Seventh Day of July, 1998

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,698,529
DATED : December 16, 1997
INVENTOR(S) : Alakhov, et al.

It is certified that error appears in the above-identified patent and that said Letters Patent is hereby corrected as shown below:

On the title page, item [75], should read :

"Valery Yu. Alakhov, Baie d'Urfe, Quebec, Canada; Alexander V. Kabanov, Omaha, Nebraska, USA; Peter G. Sveshnikov,; Eugenii S. Severin, both of Moscow, Russian Federation In the Assignee, item [73], should read "Supratek Pharma Inc., Montreal, Quebec, Canada Signed and Sealed this Eighteenth Day of May, 1999

Attest:

Q. TODD DICKINSON

*Attesting Officer*     *Acting Commissioner of Patents and Trademarks*